(12) United States Patent
Park

(10) Patent No.: US 10,980,577 B2
(45) Date of Patent: Apr. 20, 2021

(54) SPINAL DEFORMITY DEROTATION INSTRUMENT

(71) Applicant: Aesculap Implant Systems, LLC, Center Valley, PA (US)

(72) Inventor: Jacob Park, Center Valley, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 210 days.

(21) Appl. No.: 16/371,836

(22) Filed: Apr. 1, 2019

(65) Prior Publication Data

US 2020/0305932 A1 Oct. 1, 2020

(51) Int. Cl.
*A61B 17/70* (2006.01)

(52) U.S. Cl.
CPC ........ *A61B 17/708* (2013.01); *A61B 17/7091* (2013.01); *A61B 17/7032* (2013.01); *A61B 17/7085* (2013.01)

(58) Field of Classification Search
CPC ................ A61B 17/7074–7091; A61B 17/70
See application file for complete search history.

(56) References Cited

U.S. PATENT DOCUMENTS

| | | | |
|---|---|---|---|
| 7,454,939 B2 | 11/2008 | Garner et al. | |
| 2013/0110124 A1* | 5/2013 | Gleason | A61B 17/7088 606/104 |
| 2014/0180298 A1* | 6/2014 | Stevenson | A61B 17/708 606/104 |
| 2019/0069934 A1* | 3/2019 | Mickiewicz | A61B 17/7082 |

* cited by examiner

*Primary Examiner* — Eduardo C Robert
*Assistant Examiner* — Michelle C Eckman

(57) ABSTRACT

A surgical instrument for correcting spinal deformities includes a tubular body adapted to receive a second instrument through the tubular body. The tubular body forms a transverse passage adapted to receive a longitudinal fixation element through the tubular body. The tubular body further includes first and second arms for connecting the surgical instrument to a vertebral anchor. The first and second arms include one or more anti-splaying features adapted to mate with anti-splaying features on the second instrument to prevent the first and second arms from splaying as the second instrument is inserted into the tubular body.

25 Claims, 9 Drawing Sheets

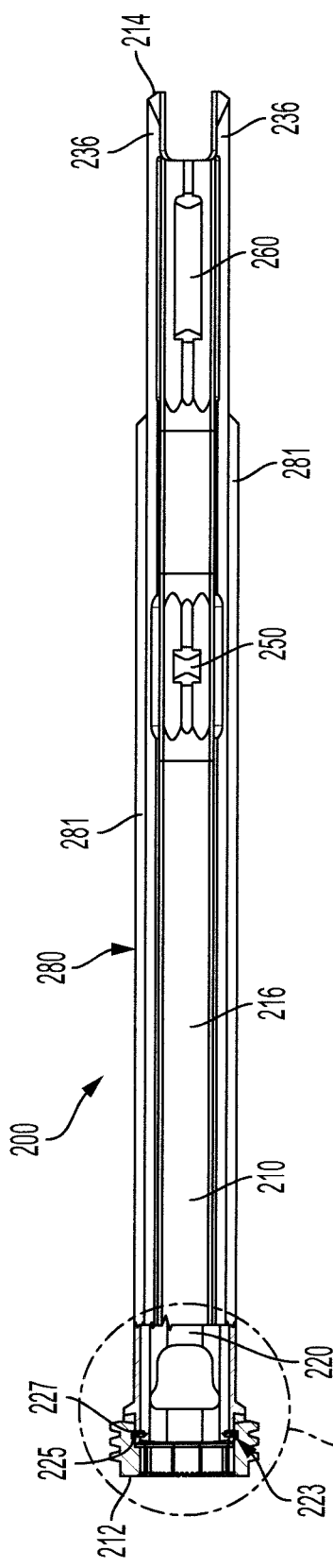
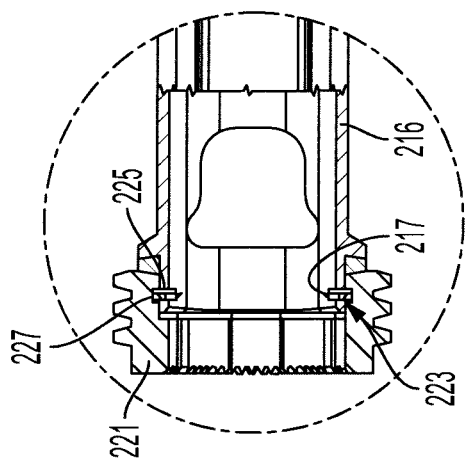
FIG. 11
FIG. 11A

SPINAL DEFORMITY DEROTATION INSTRUMENT

FIELD

The present disclosure relates generally to instruments for correcting spinal deformities and more particularly to an instrument for performing derotation maneuvers in conjunction with other procedures.

BACKGROUND

As is disclosed in U.S. Pat. No. 7,454,939, which is incorporated by reference herein, spinal fixation systems may be used in surgery to align, adjust and/or fix portions of the spinal column, i.e., vertebrae, in a desired spatial relationship relative to each other. Many spinal fixation systems employ a spinal fixation rod for supporting the spine and for properly positioning components of the spine for various treatment purposes. The spinal rod, which is generally formed of a metal, such as cobalt chrome or titanium, may be implanted to correct deformities, prevent movement of vertebral bodies relative to each other, or for other purposes. Vertebral anchors comprising pins, bolts, screws, and hooks, engage the vertebrae and connect the rod to different vertebrae.

Adult Spinal Deformity (ASD) refers to a number of conditions of the spine in which the spinal curvature is outside of defined normal limits. In some patients, the deformity is measured in degrees of rotation from a specific plane, such as the sagittal plane. "Derotation" refers to a procedure for adjusting the rotation and correcting abnormal spinal curvatures. In a derotation procedure, one or more instruments are used to apply bending moments to one or more vertebral anchors implanted in vertebral bodies. A bending moment induces rotational and translational movement of a vertebral body relative to adjacent bodies. Each vertebral anchor is implanted deep within an incision, making it difficult to apply force directly to the anchor. Therefore, a bending moment is commonly applied indirectly to a vertebral anchor by applying derotation force to a long extension tube attached to the vertebral anchor that extends above the incision.

Extension tubes can perform multiple functions aside from applying derotation force to a vertebral anchor. For example, an extension tube can provide a hollow conduit into which a second instrument can be inserted to access the vertebral anchor before or after derotation. Occasionally, the insertion of a second instrument into an extension tube results in outward force on the extension tube that causes outward deflection of the extension tube arms. This outward deflection, which will be referred to herein as "splaying", can cause extension tube arms to disconnect from the vertebral anchor and interrupt a surgical procedure.

SUMMARY

Derotation instruments according to the present description provide multifunctional extension tubes that resist splaying when other instruments are inserted into them. These derotation instruments can include features that cooperatively engage with features on other instruments to prevent attachment arms on the derotation instrument from splaying and detaching from the vertebral anchor.

Derotation instruments according to the present description can be used not only to perform derotation maneuvers, but also to position fixation elements (e.g. spinal fixation rods) in a fixation element receiver and lock the fixation element receiver to a vertebral anchor. In addition, derotation instruments according to the present description can provide portals that allow other instruments to access vertebral anchors.

In one beneficial aspect of the disclosure, an instrument for correcting spinal deformities includes a surgical instrument for correcting spinal deformities, the surgical instrument including a tubular body having a proximal end, a distal end opposite the proximal end, and a midsection extending between the proximal end and the distal end. The tubular body defines a longitudinal axis and a longitudinal passage extending along the longitudinal axis from the proximal end to the distal end, the longitudinal passage adapted to receive a second instrument through the tubular body.

In another beneficial aspect of the disclosure, the tubular body can further define a first longitudinal slot and a second longitudinal slot opposite the first longitudinal slot. The first longitudinal slot and the second longitudinal slot can terminate at the distal end of the tubular body and form a transverse passage through the tubular body. The transverse passage can be adapted to receive a longitudinal fixation element through the tubular body.

In another beneficial aspect of the disclosure, the tubular body can further include a first extension and a second extension opposite the first extension. The first extension is separated from the second extension by the first longitudinal slot and the second longitudinal slot. The first extension can include a first pivot arm for detachably connecting the surgical instrument to a first connector on the vertebral anchor, and a second pivot arm for detachably connecting the surgical instrument to a second connector on the vertebral anchor. The first pivot arm can include a first activation end and a first attachment end opposite the first activation end, and the second pivot arm can include a second activation end and a second attachment end opposite the second activation end.

In another beneficial aspect of the disclosure, the first pivot arm can define a first anti-splaying slot extending from the first activation end to the first attachment end. The first anti-splaying slot can be open to the longitudinal passage and adapted to receive a first anti-splaying element on the second instrument. The second pivot arm can define a second anti-splaying slot extending from the second activation end to the second attachment end. The second anti-splaying slot can be open to the longitudinal passage and adapted to receive a second anti-splaying element on the second instrument.

In another beneficial aspect of the disclosure, the tubular body can define a first elongated aperture, at least a portion of which extends into the first extension, and a second elongated aperture, at least a portion of which extends into the second extension.

In another beneficial aspect of the disclosure, the first pivot arm can be pivotally mounted in the first elongated aperture and the second pivot arm can be pivotally mounted in the second elongated aperture.

In another beneficial aspect of the disclosure, the first pivot arm can be mounted in the first elongated aperture by a first pivot connection, and the second pivot arm can be mounted in the second elongated aperture by a second pivot connection.

In another beneficial aspect of the disclosure, the first activation end of the first pivot arm can be connected to the first attachment end by a first dog leg section, and the second activation end of the second pivot arm can be connected to the second attachment end by a second dog leg portion.

In another beneficial aspect of the disclosure, the first anti-splaying slot can define a first aperture in the first dog leg section facing the proximal end of the tubular body, the first aperture configured to axially receive the first anti-splaying element on the second instrument.

In another beneficial aspect of the disclosure, the second anti-splaying slot can define a second aperture in the second dog leg section facing the proximal end of the tubular body, the second aperture configured to axially receive the second anti-splaying element on the second instrument.

In another beneficial aspect of the disclosure, the first pivot arm can be connected to the first pivot connection at the first dog leg section, and the second pivot arm can be connected to the second pivot connection at the second dog leg section.

In another beneficial aspect of the disclosure, the first pivot arm and the second pivot arm can be pivotally displaceable relative to the tubular body between an attachment position, in which the first attachment end and the second attachment end are attachable to the vertebral anchor, and a release position, in which the first attachment end and the second attachment end are removable from the vertebral anchor.

In another beneficial aspect of the disclosure, the first activation end of the first pivot arm can be closer to the longitudinal axis in the release position than in the attachment position, and the second activation end of the second pivot arm can be closer to the longitudinal axis in the release position than in the attachment position.

In another beneficial aspect of the disclosure, a first biasing element can bias the first pivot arm toward the attachment position, and a second biasing element can bias the second pivot arm toward the attachment position.

In another beneficial aspect of the disclosure, the first biasing element can include a first spring that exerts a first radially outward biasing force on the first activation end of the first pivot arm, and the second biasing element can include a second spring that exerts a second radially outward biasing force on the second activation end of the second pivot arm.

In another beneficial aspect of the disclosure, the first pivot arm and the second pivot arm can be pivotally displaceable against the first radially outward biasing force and the second radially outward biasing force, and toward the release position, in response to radially inward forces applied to the first activation end and the second activation end of the first pivot arm and the second pivot arm, respectively.

In another beneficial aspect of the disclosure, pivotal displacement of the first pivot arm and the second pivot arm to the release position can compress the first spring and the second spring under stored energy.

In another beneficial aspect of the disclosure, the first activation end of the first pivot arm can include a first recess that receives the first spring, and the second activation end of the second pivot arm can define a second recess that receives the second spring.

In another beneficial aspect of the disclosure, the first activation end of the first pivot arm can project radially outwardly from the first aperture when the first pivot arm is in the attachment position, and the second activation end of the second pivot arm can project radially outwardly from the second aperture when the second pivot arm is in the attachment position.

In another beneficial aspect of the disclosure, the first aperture can include a first stop for limiting pivotal displacement of the first pivot arm beyond the attachment position and a second stop for limiting pivotal displacement of the first pivot arm beyond the release position.

In another beneficial aspect of the disclosure, the first attachment end of the first pivot arm can extend into the longitudinal passage when the first pivot arm is displaced to the attachment position, and the second attachment end of the second pivot arm can extend into the longitudinal passage when the second pivot arm is displaced to the attachment position.

In another beneficial aspect of the disclosure, the first attachment end of the first pivot arm can be outside of the longitudinal passage when the first pivot arm is displaced to the release position, and the second attachment end of the second pivot arm can be outside of the longitudinal passage when the second pivot arm is displaced to the release position.

In another beneficial aspect of the disclosure, the proximal end of the tubular body can include a connection element for axially guiding the second instrument inside the longitudinal passage.

BRIEF DESCRIPTION OF THE DRAWINGS

The foregoing summary and the following detailed description will be better understood in conjunction with non-limiting examples shown in the drawing figures, of which:

FIG. 11 is another side view of the insert pusher instrument of FIG. 7 shown in partial cross section; and FIG. 11A is an enlarged view of an area of the insert pusher instrument shown in FIG. 11.

DETAILED DESCRIPTION

Figure 1:
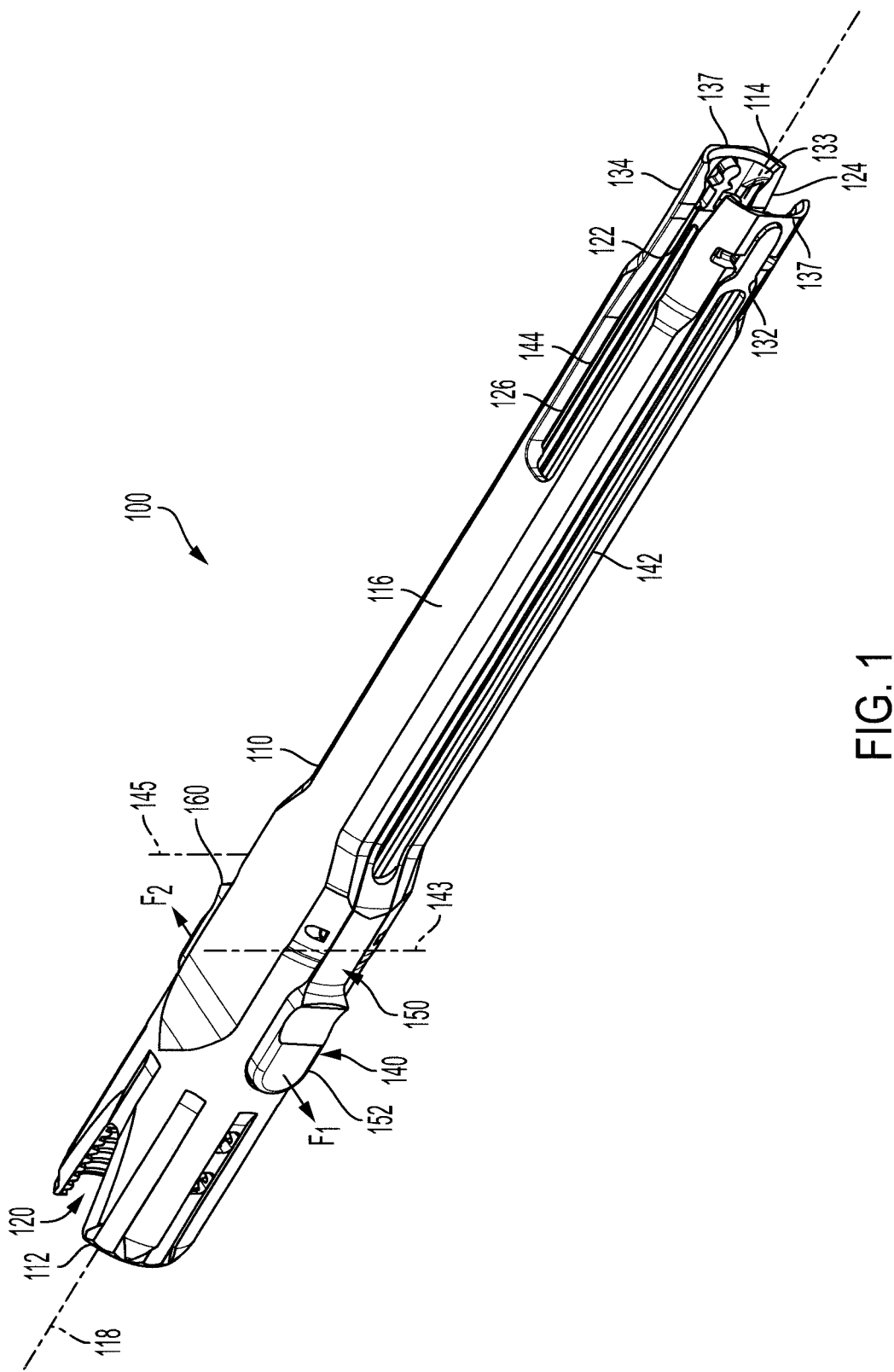
FIG. 1 is a perspective view of a derotation instrument according to one embodiment.
Figure 2:
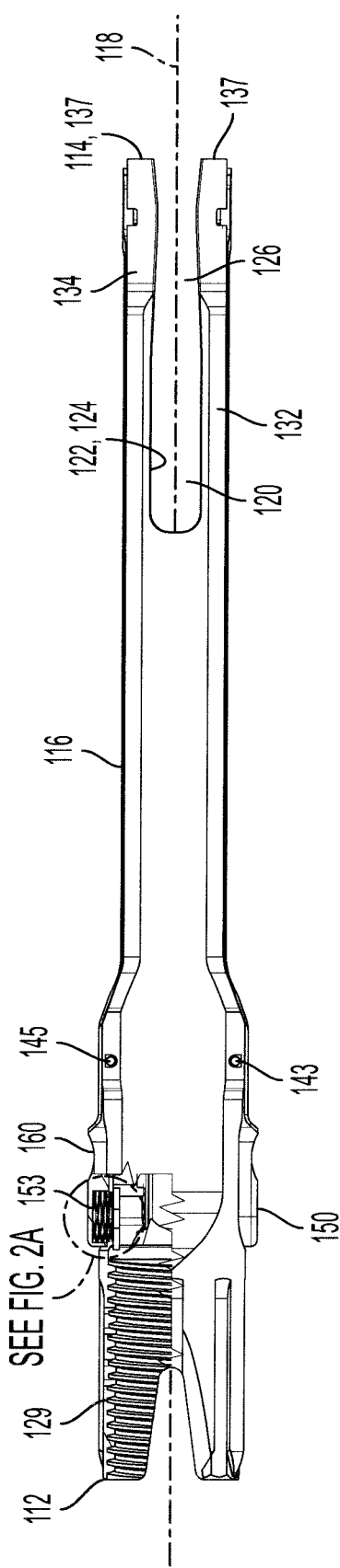
FIG. 2 is a side view of the derotation instrument of FIG. 1, shown in partial cross section.

Referring to FIGS. 1 and 2, a derotation instrument 100 is shown in accordance with one embodiment. Derotation instrument 100 is configured for detachable connection to a vertebral anchor implanted in a vertebral body to perform corrective adjustments to the spine and subsequently secure a fixation element to the vertebral anchor. For example, derotation instrument 100 is operable to induce a bending moment in a vertebral anchor in order to adjust the curvature of the spine. This can be accomplished by connecting derotation instrument 100 to the vertebral anchor, and manually applying derotation force. A surgeon can manually apply derotation force directly to the derotation instrument, or indirectly to the derotation instrument through another instrument or accessory attached to the derotation instrument. The derotation force is transferred to the vertebral body through the derotation instrument and vertebral anchor. The term "derotation force", as used herein, refers to a force applied manually by a spinal surgeon or other user that induces a bending moment in a vertebral body to correct an abnormal curvature of the spine. The term "force applying instrument", as used herein, refers to an instrument configured to apply a derotation force, which can be the derotation instrument itself, or an instrument or accessory attached to a derotation instrument. Force applying instruments can also be configured to perform other functions before, during and/or after applying derotation force.

As will be explained, derotation instrument 100 can be used with another instrument to temporarily lock a rod receiver to a bone screw. Derotation instrument 100 can also be used with a rod persuader instrument to perform rod persuasion. Moreover, derotation instrument 100 can be used as a portal that allows other instruments to access a vertebral anchor to which the derotation instrument is attached. In some applications, derotation instrument 100 can be operated in conjunction with one or more other derotation instruments attached to other vertebral bodies in the spine.

Derotation instrument 100 includes a tubular body 110 having a proximal end 112, a distal end 114 opposite the proximal end, and a midsection 116 extending between the proximal end and the distal end. Tubular body 110 defines a longitudinal axis 118 and a longitudinal passage 120 extending along the longitudinal axis. Longitudinal passage 120 extends from proximal end 112 of tubular body 110 to distal end 114.

Tubular body 110 defines a first longitudinal slot 122 and a second longitudinal slot 124 opposite the first longitudinal slot. First longitudinal slot 122 and second longitudinal slot 124 terminate at distal end 114 of tubular body 110 and form a transverse passage 126 through the tubular body. Transverse passage 126 is adapted to receive a longitudinal fixation element, such as a spinal fixation rod, through the tubular body. Derotation instrument 100 can be used with the aid of other instrumentation to insert a longitudinal fixation element into a vertebral anchor, position the longitudinal fixation element in the vertebral anchor, and secure the longitudinal fixation element in the vertebral anchor with a locking element.

Tubular body 110 also includes a first extension 132 and a second extension 134 opposite the first extension. First extension 132 and second extension 134 merge with midsection 116 of tubular body 110 and have free ends 137 that terminate at distal end 114. First extension 132 is separated from second extension 134 by first longitudinal slot 122 and second longitudinal slot 124.

First and second extensions according to the present disclosure are configured to detachably connect to vertebral anchors. For example, first and second extensions according to the present disclosure can be configured to detachably connect to a rod receiver or "tulip" component associated with a vertebral anchor. In this regard, the first and second extensions can have inner geometries adapted to conform to outer geometries of the vertebral anchor. For example, the extensions can be arcuate shaped extensions with concave interior surfaces that conform to a round outer geometry associated with a rod receiver or tulip component of the vertebral anchor. In the present example, first extension 132 and second extension 134 each form a partial cylinder with a concave interior surface 133 that conforms to the circular outer geometry of a rod receiver of a vertebral anchor. In this configuration, first extension 132 and second extension 134 are configured to receive the rod receiver between them and securely clamp onto the rod receiver.

First and second extensions 132, 134 include a coupling mechanism 140 configured to lock and unlock the clamping engagement between the first and second extensions and the vertebral anchor. Coupling mechanism 140 includes a first pivot arm 150 for detachably coupling first extension 132 to a first connector on the vertebral anchor. Coupling mechanism 140 also includes a second pivot arm 160 for detachably connecting the second extension 134 to a second connector on the vertebral anchor. Pivot arms according to the present disclosure can be mounted to the tubular body in a number of arrangements. In the present example, tubular body 110 defines a first elongated aperture 142, a portion of which extends into first extension 132, and a second elongated aperture 144, a portion of which extends into the second extension 134. First pivot arm 150 is pivotally mounted in first elongated aperture 142, and second pivot arm 160 is pivotally mounted in second elongated aperture 144. In particular, first pivot arm 150 is configured to pivot through the first elongated aperture 142 about a first pivot axis 143, and second pivot arm 160 is configured to pivot through second elongated aperture 144 about a second pivot axis 145. First pivot axis 143 and second pivot axis 145 are parallel to one another, and perpendicular to longitudinal axis 118 of tubular body 110.

Figure 3:
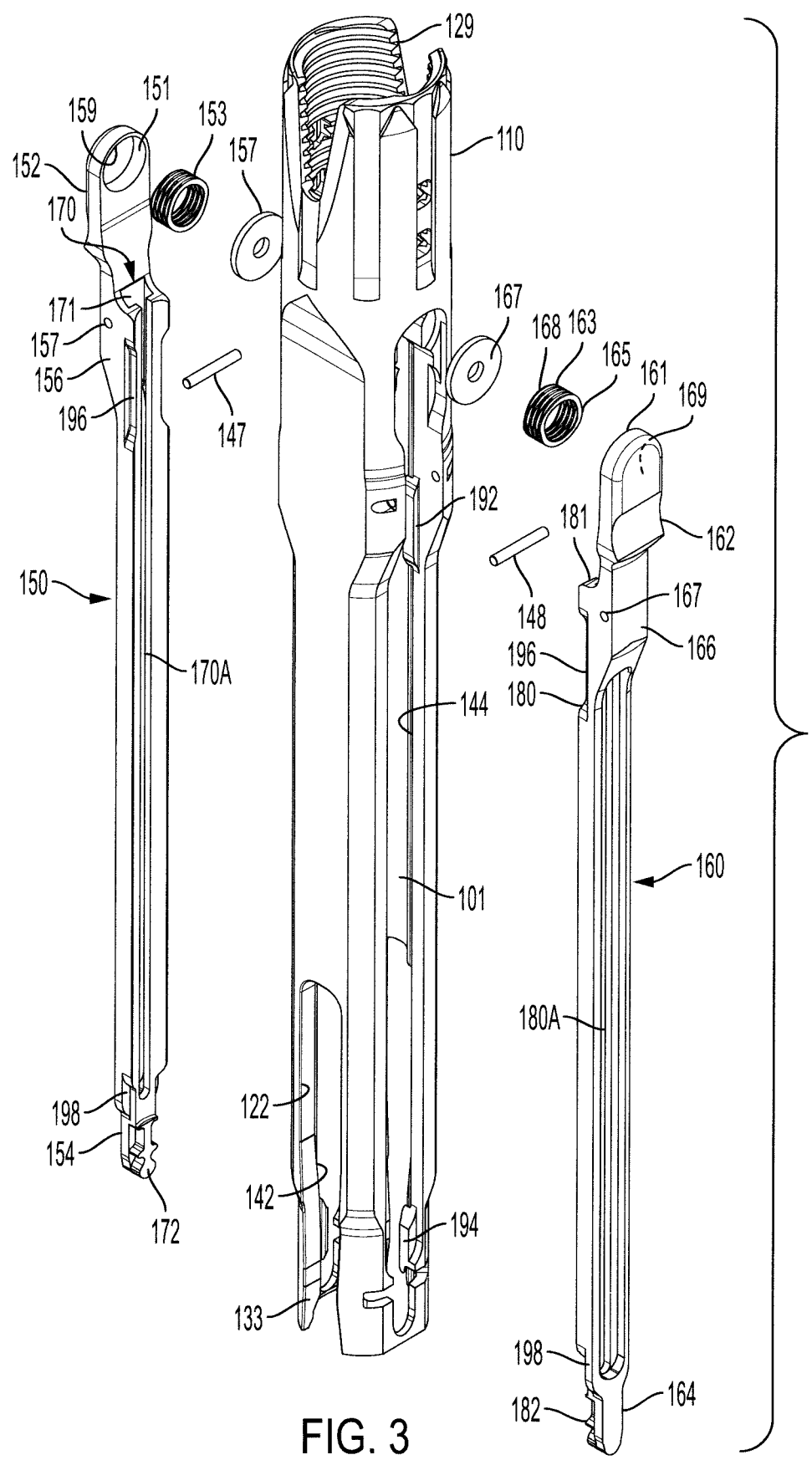
FIG. 3 is an exploded perspective view of the derotation instrument of FIG. 1.

Referring to FIG. 3, additional details of derotation instrument 100 and its components are shown. First pivot arm 150 has a first activation end 152 and a first attachment end 154 opposite the first activation end. Similarly, second pivot arm 160 has a second activation end 162 and a second attachment end 164 opposite the second activation end. First pivot arm 150 is mounted in first elongated aperture 142 by a first pivot connection in the form of a pin 147 that crosses the first elongated aperture. Second pivot arm 160 is mounted in the second elongated aperture 144 by a second pivot connection in the form of a pin 148 that crosses the second elongated aperture.

First activation end 152 of first pivot arm 150 is connected to first attachment end 154 by a first dog leg section 156. Second activation end 162 of second pivot arm 160 is connected to the second attachment end 164 by a second dog leg portion 166. First dog leg section 156 defines a through-bore 157 adapted to receive pin 147 to mount first pivot arm 150 in first elongated aperture 142. Second dog leg section 166 defines a through-bore 167 adapted to receive pin 148 to mount second pivot arm 160 in second elongated aperture 152. In this arrangement, first pivot arm 150 and second pivot arm 160 are pivotable about pin 147 and pin 148, respectively. That is, first pivot arm 150 and second pivot arm 160 are held captive in the first and second elongated apertures 142, 152, respectively, but are pivotally displaceable within the first and second elongated apertures.

Figure 5:
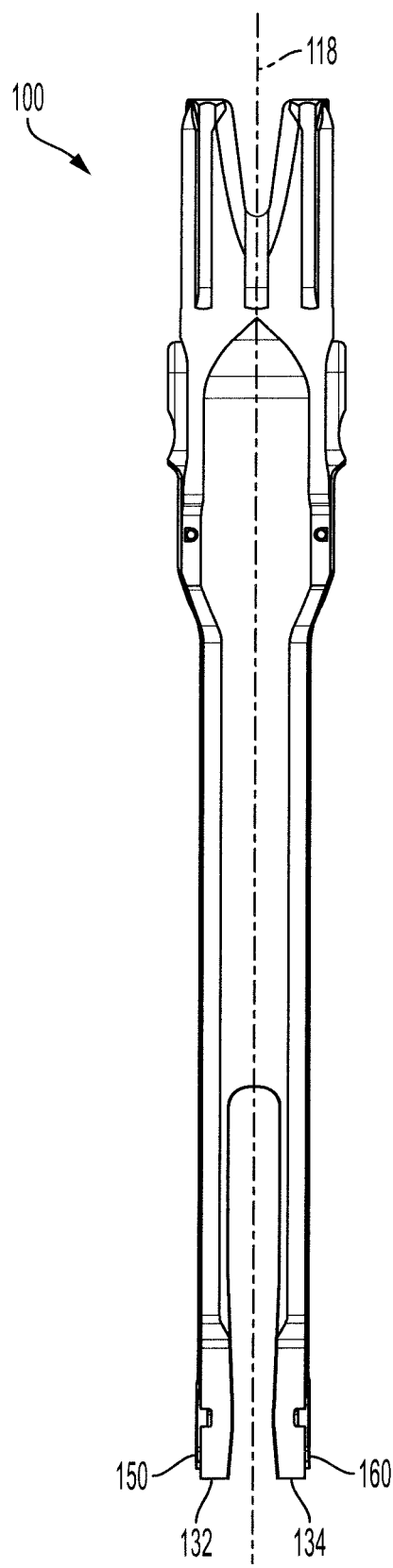
FIG. 5 is a side view of the derotation instrument of FIG. 1 in a first operative state.
Figure 6:
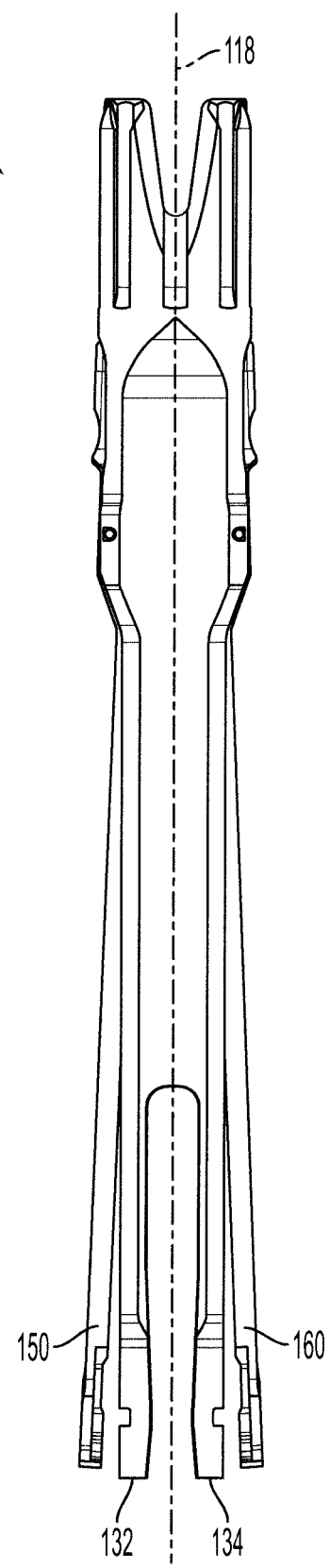
FIG. 6 is a side view of the derotation instrument of FIG. 1 in a second operative state.

First pivot arm 150 and second pivot arm 160 are independently pivotable relative to tubular body 110 between attachment positions and release positions. In the attachment positions, which are shown in FIG. 5, first and second pivot arms 150, 160 are positioned so that first attachment end 154 and second attachment end 164 are pivoted inwardly toward longitudinal axis 118 where each can engage the vertebral anchor. First attachment end 154 and second attachment end 164 engage the vertebral anchor in a form locking manner, as will be explained, to connect derotation instrument 100 to the vertebral anchor. In the release positions, which are shown in FIG. 6, first attachment end 154 and second attachment end 164 are pivoted outwardly and away from longitudinal axis 118 to allow detachment of derotation instrument 100 from the vertebral anchor. It will be appreciated from FIGS. 5 and 6 that first attachment end 154 and second attachment end 164 are closer to longitudinal axis 118 in the attachment position than in the release position. Conversely, first activation end 152 and second activation end 162 are closer to longitudinal axis 118 in the release position than in the attachment position.

Derotation instruments according to the present disclosure can be configured with one or more biasing mechanisms that maintain an attachment between attachment ends and vertebral anchors until the biasing mechanisms are released or overcome by some counterforce. In the present example, derotation instrument 100 includes a first biasing element that biases first pivot arm 150 toward the attachment position and a second biasing element that biases second pivot arm 160 toward the attachment position. Various types of biasing mechanisms can be used, including but not limited leaf springs, wave springs, torsion springs, coil springs, spring washers and other biasing elements that store and release energy upon application and removal of force.

First pivot arm 150 defines a circular blind bore or recess 151 that receives a biasing element in the form of a first spring 153. Similarly, second pivot arm 160 defines a circular blind bore or recess 161 that receives a biasing element in the form of a second spring 163. First spring 153 and second spring 163 are wave springs that are configured to store energy in response to axial compression force and release energy when the axial compression force is removed.

Figure 2A:
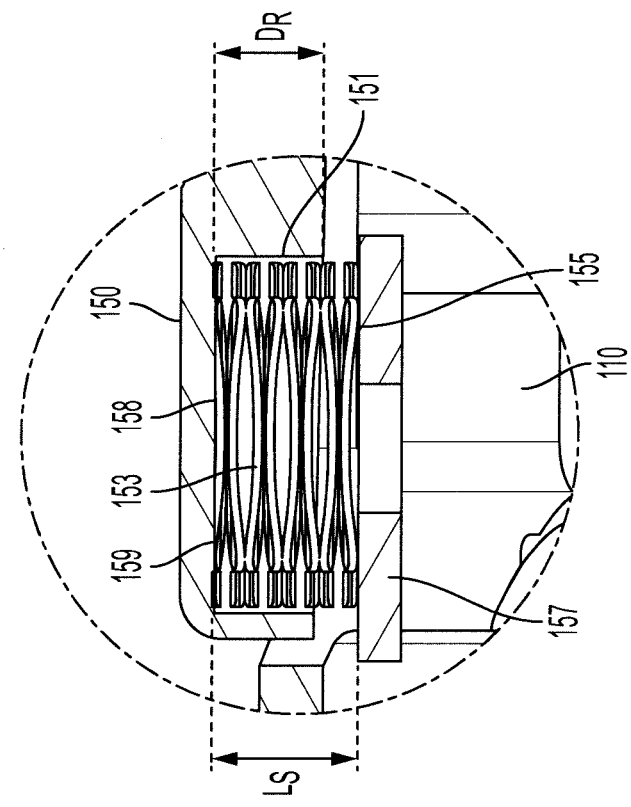
FIG. 2A is a magnified view of an area of derotation instrument shown in FIG. 2.

FIG. 2A provides an enlarged view of first spring 153 assembled inside recess 151 of first pivot arm 150. First spring 153 has a first end 155 that bears against a wall in the form of a washer 157 that is fixed inside tubular body 110. First spring 153 also has a second end 158 that bears against an interior surface or spring seat 159 inside recess 151. The axial length Ls of first spring 153 is greater than the axial depth DR of recess 151, such that the first spring projects outside of the recess when in a relaxed or uncompressed state, as shown.

Second spring 163 is assembled with second pivot arm 160 in the same arrangement and manner that first spring 153 is assembled with first pivot arm 150. Therefore, the arrangement of second spring 163 inside second pivot arm 160 appears the same as first spring 153 in first pivot arm 150 shown in FIG. 2A. As with first spring 153, second spring 163 has a first end 165 that bears against a wall in the form of a washer 167 that is fixed inside tubular body 110. Second spring 163 also has a second end 168 that bears against an interior surface or spring seat 169 inside recess 161. The axial length of second spring 163 is greater than the axial depth of recess 161, such that the second spring projects outside of the recess when in a relaxed or uncompressed state.

Referring to FIG. 1, first spring 153 is configured to exert a first radially outward biasing force $F_1$ on first activation end 152 of first pivot arm 150. Second spring 163 is configured to exert a second radially outward biasing force $F_2$ on second activation end 162 of second pivot arm 160. Biasing force $F_1$ is directed in a first radially outward direction, and biasing force $F_2$ is directed in a second radially outward direction opposite the first radially outward direction. First activation end 152 and second activation end 162 are diametrically opposed to one another relative to longitudinal axis 118, such that biasing forces $F_1$, $F_2$ have the effect of urging first attachment end 154 and second attachment end 164 toward each other, i.e. toward their respective attachment positions.

First pivot arm 150 and second pivot arm 160 are pivotally displaceable against biasing forces $F_1$, $F_2$, respectively, to displace first and second activation ends 152, 162 toward their respective release positions. That is, first activation end 152 is pivotally displaceable inwardly toward longitudinal axis 118 in response to a first inwardly directed force applied to the first activation end. Likewise, second activation end 162 is pivotally displaceable inwardly toward longitudinal axis 118 in response to a second inwardly directed force applied to the second activation end, where the direction of such force is directed more or less opposite the direction of the first inwardly directed force. The spacing between first activation end 152 and second activation end 162 is small, so as to permit a user to manually compress or squeeze the first and second activation ends together by pressing their thumb against one of the activation ends and their forefinger against the other of the activation ends.

First and second attachment ends according to the present disclosure can have various configurations for attaching to vertebral anchors. For example, the first and second pivot arms can have one or more engagement structures designed to mate with one or more complementary engagement structures on vertebral anchors. These engagement structures can take the form of bosses, pins, tabs or other regularly or irregularly-shaped protuberances, with or without spring biasing mechanisms, that releasably engage bores, slots, cut outs or other regularly or irregularly-shaped voids. It will be understood that any such protuberances can be formed on the pivot arms and any such voids can be formed on the vertebral anchor, or vice versa.

Figure 4:
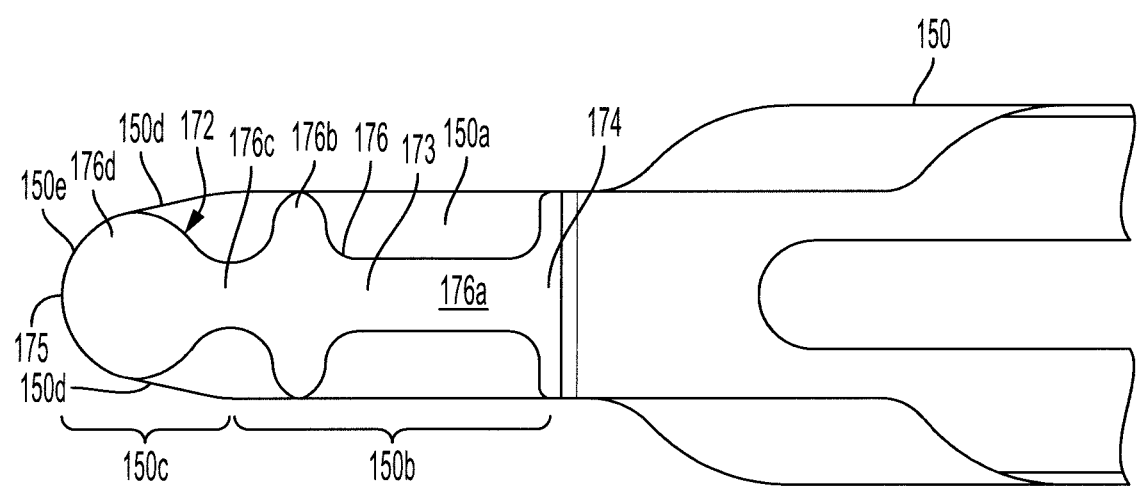
FIG. 4 is an enlarged truncated side view of a distal section of one of the components of the derotation instrument of FIG. 1.

Referring to FIGS. 3 and 4, first and second attachment ends 154, 164 have engagement structures in the form of first and second locking tabs 172, 182, respectively. First and second locking tabs 172, 182 are configured identically, and are arranged in a mirror arrangement, as with the other features of first and second pivot arms 150, 160. For brevity, only the details of first locking tab 172 will be described, with the understanding that the same description applies to second locking tab 182.

First locking tab 172 has an irregularly-shaped tab body 173 that projects radially inwardly from an adjoining section 150a of first pivot arm 150. Adjoining section 150a of first pivot arm 150 has a constant width section 150b that transitions to a tapered end section 150c. Tapered end section 150c has two linear sides 150d that transition to a rounded end 150e. Tab body 173 has a proximal end 174, a distal end 175, and a midsection 176 between the proximal end and distal end. Midsection 176 includes a narrow section 176a of constant width that is narrower than the width of constant width section 150b of adjoining section 150a. Narrow section 176a transitions to a widened section 176b that has the same width as constant width section 150b of adjoining section 150a. Widened section 176b transitions to a narrower neck portion 176c which has a width that is narrower than the width of constant width section 150b of adjoining section 150a. Finally, neck portion 176c transitions to a circular end portion 176d having a portion of its perimeter contiguous with rounded end 150e of adjoining section 150a.

Tab body 173 is configured to be inserted into a first cut-out in an exterior side wall of a rod receiver of a vertebral anchor. The cut-out is adapted to receive tab body 173 in a keyed arrangement as first pivot arm 150 is pivoted toward longitudinal axis 118 to the attachment position. The shape of the cut-out can be identical to some of the aforementioned sections of tab body 173, or all of the sections. In either case, the shape of the cut-out can have sections that narrow and widen so as to fit in a form-locking manner around the narrow section 176a, widened section 176b, neck portion 176c and/or end portion 176d. Once tab body 173 is pivoted into the cut-out to assume the attachment position, the outer walls of the tab body abut the inner walls of the cut-out in form-locking engagement to prevent the tab body from moving in the cut out in any direction, except the outward direction in response to pivotal displacement of the first pivot arm 150 toward the release position.

The vertebral anchor can have a second cut out adapted to receive second locking tab 182 of second pivot arm 160 in an identical arrangement and manner as described above regarding the first locking tab 172.

First and second pivot arms 150, 160 are thus responsible for locking derotation instrument 100 to a vertebral anchor.

Figure 7:
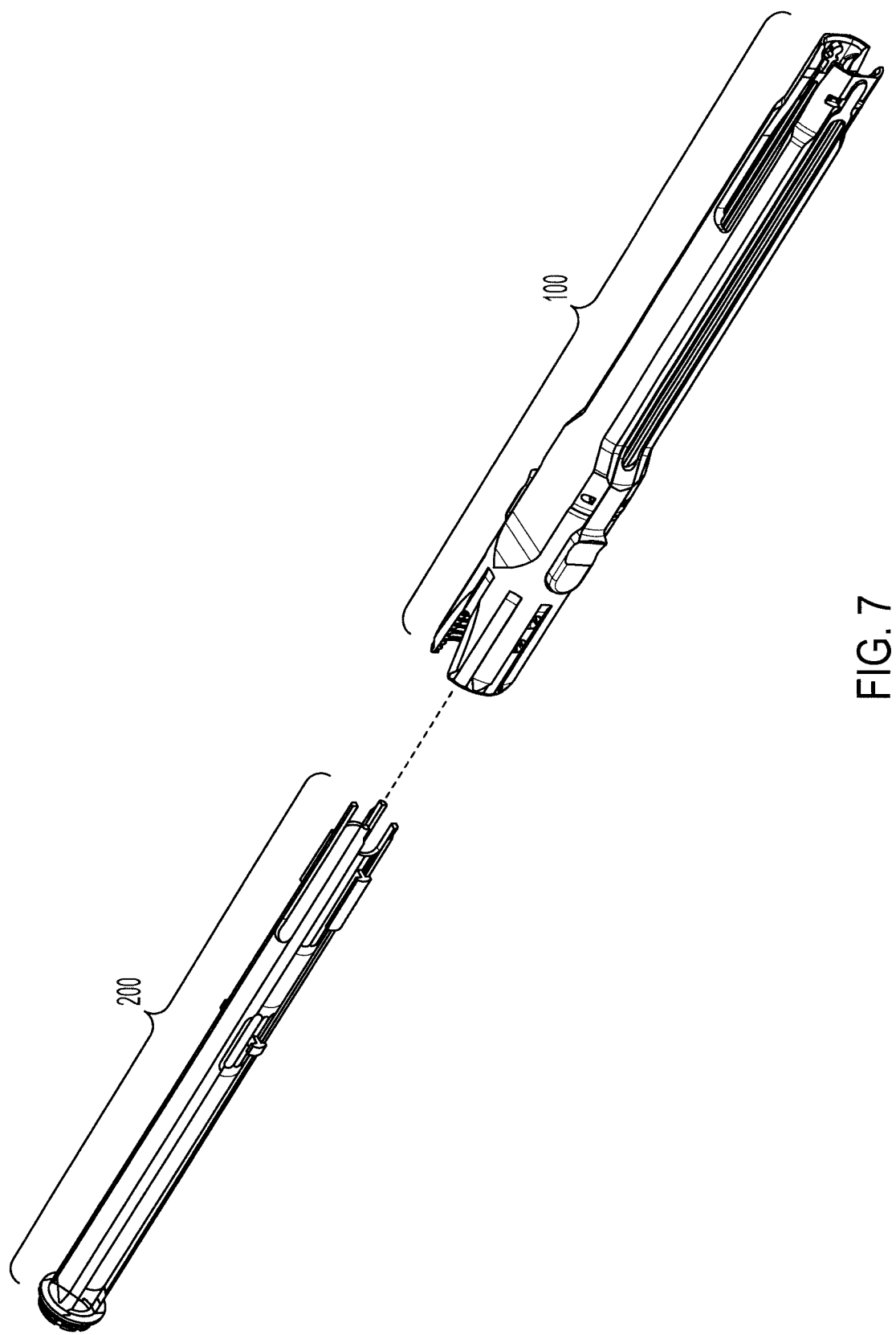
FIG. 7 is a perspective view of the derotation instrument of FIG. 1 and a separate insert pusher instrument that can be used with the derotation instrument.

Referring now to FIG. 7, derotation instrument 100 is shown with a second instrument in the form of an insert pusher instrument or "insert pusher" 200. The main purpose of insert pusher 200 is to provisionally lock the position of a rod receiver relative to the position of the bone screw on a vertebral anchor, without inserting a rod and locking screw (e.g. set screw) into the vertebral anchor. This is performed as a temporary locking procedure that disables polyaxial rotation of the rod receiver about the bone screw (called "polylocking"). Once polylocking is performed, the bone screw and rod receiver form a singular fixed construct, allowing adjustment force to be applied to both the rod receiver and bone screw in unison.

Figure 8:
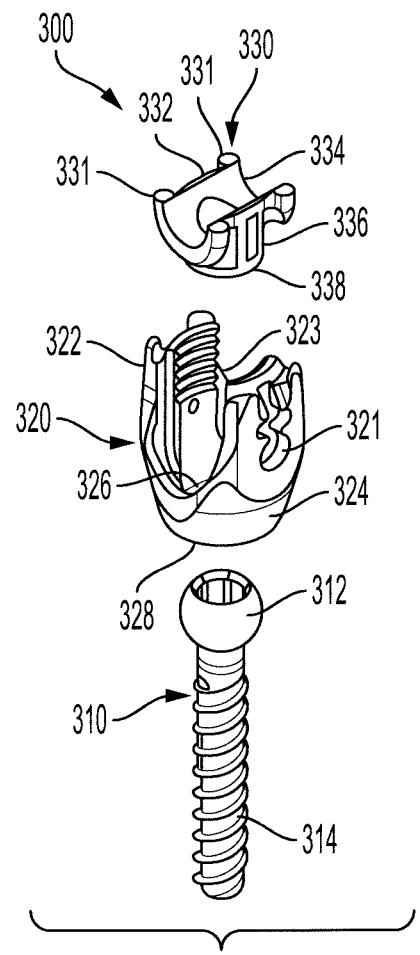
FIG. 8 is an exploded perspective view of a vertebral anchor that can be used with the derotation instrument of FIG. 1.
Figure 9:
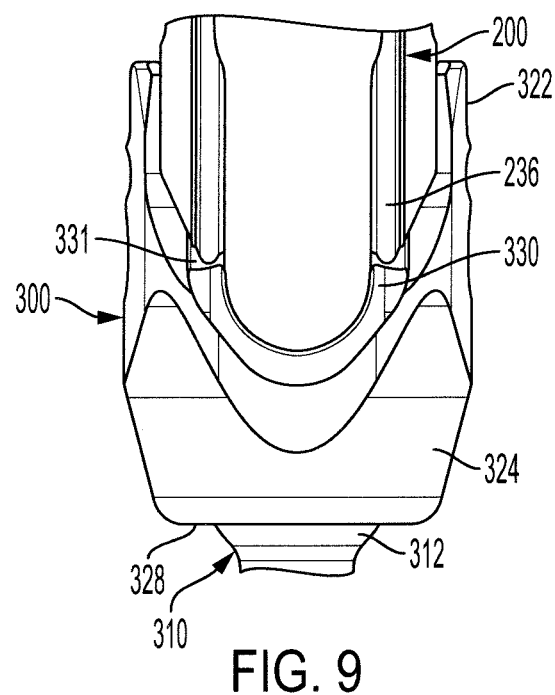
FIG. 9 is a magnified view of distal ends of the insert pusher instrument of FIG. 7 and vertebral anchor of FIG. 8, with a portion of the vertebral anchor cut away.

FIGS. 8 and 9 show one example of a vertebral anchor 300 that can be used with derotation instruments and insert pushers according to the present disclosure. Vertebral anchor 300 includes a polyaxial bone screw 310 with a spherical shaped screw head 312 and threaded shank 314. Bone screw 310 is configured to be received in rod receiver 320. Rod receiver 320 has an upper portion 322 that defines a U-shaped channel 323 to receive an elongated fixation element, such as a spinal rod. Rod receiver 320 also has a lower portion 324 that defines a spherical seat 326 in its interior and a through-hole 328. Through-hole 328 has a diameter that is smaller than the diameter of screw head 312. Rod receiver 320 is therefore configured to receive bone screw 320 in a seated arrangement, with screw head 312 seated in spherical seat 326, and with threaded shank 314 projecting out of through-hole 328.

Rod receiver 320 has a pair of diametrically opposed cut-outs 321 that are open on the exterior of the rod receiver, and that extend into the wall of the rod receiver. Cut-outs 321 have irregular shapes that conform to the irregular shapes of locking tabs 172, 182 on derotation instrument 100.

Vertebral anchor 300 also includes an insert 330. Insert 330 has an upper portion 332 that defines a U-shaped recess 334 to receive an elongated fixation element, such as a spinal rod. Insert 330 also has a lower portion 336 with a spherical shaped concavity 338. When vertebral anchor 300 is assembled, insert 330 is positioned in rod receiver 320 in a position proximal to screw head 312. In this position, recess 334 is positioned to receive an elongated fixation element, such as a spinal rod, and concavity 338 is positioned to bear against and frictionally engage screw head 312.

FIG. 9 shows a cross sectional view of insert pusher 200 inside vertebral anchor 300 and in engagement with insert 330. Insert pusher 200 is operable to lock the position of rod receiver 320 by applying axial force on insert 330. To accomplish this, insert pusher 200 has four pusher posts 236 that engage landings 331 on the top of insert 330. Axial force on landings 331 compresses the insert into frictional engagement with screw head 312 of bone screw 310. The frictional engagement is sufficient to stabilize rod receiver 320 on screw head 312 so that the rod receiver does not pivot or "flop" on bone screw 310.

Once the rod receiver and polyaxial screw are polylocked, derotation instrument can be used to apply a derotation force to the vertebral anchor. Polylocking of the vertebral anchor is helpful when applying derotation force, but is not necessary. Therefore, it is contemplated that derotation instrument 100 can be used to apply derotation force on vertebral anchor 300 without polylocking and without insert pusher 200 in place.

When derotation is performed with insert pusher 200 in place, the derotation force applied to derotation instrument 100 is transferred to the polylocked rod receiver 320 and bone screw 310 to adjust the position of the vertebral body.

Figure 10:
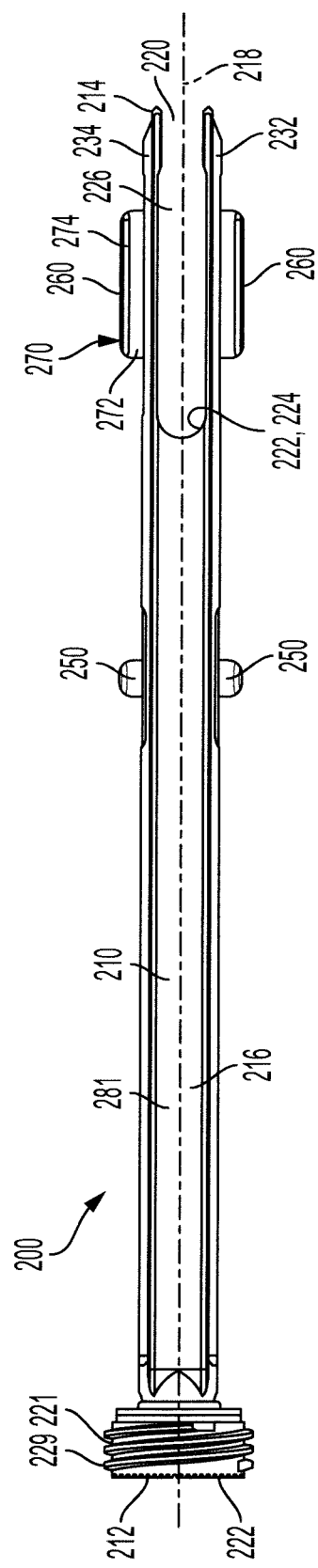
FIG. 10 is side view of the insert pusher instrument of FIG. 7.

Features of insert pusher 200 are shown in more detail in FIGS. 10-11A. Insert pusher 200 includes a tubular body 210 having a proximal end 212, a distal end 214 opposite the proximal end, and a midsection 216 extending between the proximal end and the distal end. Tubular body 210 defines a longitudinal axis 218 and a longitudinal passage 220 extending along the longitudinal axis. Longitudinal passage 220 extends from proximal end 212 of tubular body 210 to distal end 214.

Tubular body 210 defines a first longitudinal slot 222 and a second longitudinal slot 224 opposite the first longitudinal slot. First longitudinal slot 222 and second longitudinal slot 224 terminate at distal end 214 of tubular body 210 and form a transverse passage 226 through the tubular body. As with transverse passage 126 of derotation instrument 100, transverse passage 226 is adapted to receive a longitudinal fixation element, such as a spinal fixation rod, through the tubular body. Tubular body 210 also includes a first extension 232 and a second extension 234 opposite the first extension. First extension 232 is separated from second extension 234 by first longitudinal slot 222 and second longitudinal slot 224. In addition, first extension 232 and second extension 234 merge with midsection 216 of tubular body and terminate at distal end 214. Each of first extension 232 and second extension 234 has a pair of pusher posts 236. As explained above, pusher posts 236 are configured to apply axial force to an insert in a vertebral anchor to polylock the position and orientation of the rod receiver relative to the bone screw.

Proximal end 212 of insert pusher 200 has a connector ring 221 that is configured to connect insert pusher 200 to the interior of derotation instrument 100. Connector ring 221 is also operable to axially displace the insert pusher inside the derotation instrument, and maintain the insert pusher in a coaxially aligned relationship with derotation instrument. Connector ring 221 is connected to midsection 216 of insert pusher 200 by a rotatable coupling 223. Referring to FIG. 11A, rotatable coupling 223 includes a snap ring 225 that is partially received in an annular groove 227 inside connector ring 221 and partially received in a circumferential groove 217 in midsection 216. In this arrangement, connector ring 221 is rotatable relative to midsection 216 and distal end 214 of insert pusher 200, but axially fixed to the midsection and distal end.

Connector ring 221 has a toothed surface 222 configured to engage a similarly toothed surface of another instrument, which may be coupled to the connector ring to apply torque to insert pusher 220. Connector ring 221 also has a male thread 229 extending around its circumference. Male thread 229 is configured to mate with a female thread 129 inside proximal end 112 of derotation instrument 100, the female thread shown in FIGS. 2 and 3. When male thread 229 is mated with female thread 129, insert pusher 200 is axially displaceable and guided inside longitudinal passage 120 in response to rotation of connector ring 221. The engagement between male thread 229 and female thread 129 maintains insert pusher 200 in coaxial alignment with derotation instrument 100. This alignment, and the pre-aligned arrangements of pusher posts 236 and the insert in the polyaxial screw, ensure that the pusher posts contact the appropriate sections of the insert to apply axial force and lock the rod receiver on the pedicle screw.

Insert pushers and derotation instruments in accordance with the present disclosure can have one or more mechanisms that prevent the first and second pivot arms from splaying when the instruments are combined. If not prevented, splaying can disconnect the first and second pivot arms from the vertebral anchor and interrupt a surgical procedure.

The term "anti-splaying", as used herein, refers to any feature that holds the first and second pivot arms in their locked positions and prevents the locking arms from splaying. Anti-splaying mechanisms according to the present disclosure prevent the first and second pivot arms on the derotation instrument from splaying while the insert pusher is advanced into the derotation tube and into the vertebral anchor to apply polylocking force. In the present example, midsection 216 of insert pusher 200 has a first pair of anti-splaying elements in the form of locking rails 250. In addition, first and second extensions 232, 234 have a second pair of anti-splaying elements in the form of locking rails 260 that are axially aligned with locking rails 250. Locking rails 260 are longer than locking rails 250 in the axial direction.

Each locking rail 250, 260 has a T-shaped body 270 comprising a stem portion 272 that extends outwardly from tube body 210 and a flange portion 274 that extends generally perpendicular to stem portion 272. Referring again to FIG. 3, first pivot arm 150 defines a first anti-splaying slot 170 extending from first dog leg section 156 to first attachment end 154. Similarly, second pivot arm 160 defines a second anti-splaying slot 180 extending from second dog leg section 166 to second attachment end 164. First anti-splaying slot 170 and second anti-splaying slot 180 are adapted to axially receive first and second locking rails 250, 260 through their proximal ends, and allow the locking rails to slide axially to the distal ends of pivot arms 150, 160. In particular, first anti-splaying slot 170 defines a first aperture 171 in first dog leg section 156 that faces proximal end 212 of tube body 210. Second anti-splaying slot 180 similarly defines a second aperture 181 in second dog leg section 166 that faces proximal end 212 of tube body 210. First and second apertures 171, 181 are each configured to axially receive first and second locking rails 250, 260 to allow the locking rails to slide axially to the distal ends of the pivot arms 150, 160.

First anti-splaying slot 170 and second anti-splaying slot 180 define respective openings 170A, 180A that are open to longitudinal passage 120. Openings 170A, 180A receive stem portions 272 of locking rails 250, 260 when the locking rails are inserted into pivot arms 150, 160. Locking rails 250, 260 are axially positioned on insert pusher 200 so that when the insert pusher is advanced as far as possible into longitudinal passage 120 to engage insert 330 of the vertebral anchor, the locking rails prevent the distal ends of pivot arms 150, 160 from splaying or bending outwardly. This maintains pivot arms 150, 160 in a straight configuration with locking tabs 172, 182 firmly fixed in cut-outs 321 of rod receiver 320.

Derotation instrument 100 and insert pusher 200 can be operated in the following manner to adjust or correct a spinal curvature. The described manner of operation assumes that the vertebral anchor is the aforementioned vertebral anchor 300 or a similar polyaxial screw assembly. It will be understood, however, that derotation instrument 100 and insert pusher 200 can be used with other types of vertebral anchors. After vertebral anchor 300 is implanted into a vertebral body, derotation instrument 100 is attached to rod receiver 320 by lowering free ends 137 around the rod receiver so that the rod receiver is received into longitudinal passage 120 between first extension 132 and second extension 134. Derotation instrument 100 is also oriented relative to rod receiver 320 so that first and second locking tabs 172, 182 are aligned with cut-outs 321 in the exterior sides of rod receiver 320. Once first and second locking tabs 172, 182 are properly aligned with cut-outs 321, derotation instrument 100 is advanced axially over rod receiver 320 until the rod receiver is clamped between first and second extensions 132, 134.

Derotation instrument 100 can be locked in clamping engagement with rod receiver 320 in a number of ways. In a first locking method, derotation instrument 100 is advanced over rod receiver 320 with first and second pivot arms 150, 160 in the attachment position. That is, no force is applied to first activation end 152 or second activation end 162. In this condition, first attachment end 154 and second attachment end 164 are closer together as shown in FIG. 5, and they project into longitudinal passage 120. As derotation instrument 100 advances over the rod receiver 320, locking tabs 172, 182 slide into cut-outs 321 in an axial direction and lockingly engage the rod receiver.

In a second locking method, derotation instrument 100 is advanced over rod receiver 320 with first and second pivot arms 150, 160 moved to the release position. That is, a radially inward squeezing force is applied to first activation end 152 and second activation end 162 to spread first attachment end 154 and second attachment end 164 farther apart, as shown in FIG. 6. First activation end 152 projects radially outwardly from first elongated aperture 142 when first pivot arm 150 is in the attachment position. Second activation end 162 of second pivot arm 160 projects radially outwardly from second elongated aperture 144 when the second pivot arm is in the attachment position.

Pivotal displacement of first pivot arm 150 and second pivot arm 160 to the release position compresses first spring 153 and second spring 163 under stored energy, and moves first and second attachment ends 154, 164 outside of longitudinal passage 120. In this state, derotation instrument 100 can be completely advanced over the rod receiver, which can be determined by tactile feel when stopping surfaces on the derotation instrument and rod receiver contact one another, or by other means. Once derotation instrument 100 is completely advanced over the rod receiver, the inward squeezing forces on first and second activation ends 152, 162 are removed. This releases pressure on first and second springs 153, 163, allowing the springs to expand and push first and second activation ends 152, 162 radially outwardly. This in turn causes first and second attachment ends 154, 164 to pivot radially inwardly such that first and second locking tabs 172, 182 enter their corresponding cut-outs 321 in rod receiver 320. Once first and second attachment ends 154, 164 pivot in this manner, the first and second attachment ends assume their respective attachment positions in cut-outs 321 to lock derotation instrument 100 to rod receiver 320.

Derotation instruments according to the present disclosure can also include one or more features to limit the pivot motion of the first and second pivot arms when the insert pusher is not inserted into the pivot arms. This can be desirable to control the positions of the activation ends and attachment ends after pivoting, and limit the amount of force applied to the springs. For example, derotation instruments according to the present disclosure can have one or more stop elements that limit the range of pivot motion of the pivot arms. In the current example, first and second elongated apertures 142, 144 each have proximal stops 192 and distal stops 194 along each side. First and second pivot arms 150, 160 have proximal stop surfaces 196 and distal stop surfaces 198. Proximal stop surfaces 196 are configured to abut proximal stops 192 when first and second pivot arms 150, 160 are pivoted to the release positions. This limits deflection of springs 153, 163, and limits the outward displacement of first and second attachment ends 154, 164. Distal stop surfaces 198 are configured to abut distal stops 194 when first and second pivot arms 150, 160 are pivoted to the attachment positions. This limits the inward displacement of first and second attachment ends 154, 164, and limits the outward displacement of first and second activation ends 152, 162 outside of their respective elongated apertures 142, 144.

Once derotation instrument 100 is attached to the vertebral anchor, the derotation instrument can receive a force applying instrument for applying polylocking force to the vertebral anchor. For example, insert pusher 200 can be inserted into derotation instrument 100 by axially aligning tubular body 210 with longitudinal passage 120. Before advancing insert pusher 200 into derotation instrument 100, the insert pusher must be oriented in the proper orientation so that rails 250, 260 are axially aligned with first and second force transfer slots 170, 180 respectively. To this end, derotation instrument 100 and insert pusher 200 feature an orientation mechanism 280 that maintains the insert pusher in the proper orientation as it is inserted and advanced into longitudinal passage 120 of the derotation instrument.

Instruments according to the present disclosure can feature many different types of orientation mechanisms, including but not limited to unique geometric features on mating surfaces. In the present example, orientation mechanism 280 includes a pair of diametrically opposed longitudinal bars 281 that extend along tubular body 210, as shown in FIG. 11. Longitudinal bars 281 are angularly offset from rails 250 by ninety degrees. Orientation mechanism 280 also includes a pair of diametrically opposed longitudinal channels 101 that extend into the inner wall of tubular body 110. A portion of one channel 101 is shown in one side of tubular body 110 in FIG. 3, with the understanding that an identical longitudinal channel extends in the inner wall on the opposite side of the tubular body. Insert pusher 200 can only be inserted and advanced in longitudinal passage 120 of derotation instrument 100 if longitudinal bars 281 are axially aligned with longitudinal channels 101. The width of each longitudinal channel 101 is slightly wider than the width of each longitudinal bar 281. As such, longitudinal channels 101 are adapted to receive longitudinal bars 281 in a captive orientation that prevents insert pusher 200 from rotating relative to derotation instrument 100 as the former is inserted into the latter. This ensures that rails 150, 160 remain in axial alignment with first and second anti-splaying slots 170, 180 during insertion of insert pusher 200.

Although this description makes reference to specific embodiments and illustrations, the invention is not intended to be limited to the details shown. For example, it will be appreciated that derotation instruments according to the present disclosure need not work exclusively with insert pushers, but can be used with other types of instruments without an insert pusher in place. For example, derotation instruments according to the present disclosure can be configured to work with rod persuader instruments. In such assemblies, the rod persuader instruments can include locking rails that are arranged to cooperate with the pivot arms of the derotation instrument in the same manner as locking rails 250, 260 described on insert pusher 200.

Accordingly, the present disclosure encompasses various modifications and combinations of the specific embodiments and illustrations described herein, including variations that may be made within the scope and range of equivalents of the originally filed claims.

What is claimed:

1. A surgical instrument for correcting spinal deformities, the surgical instrument comprising a tubular body having a proximal end, a distal end opposite the proximal end, and a midsection extending between the proximal end and the distal end, the tubular body defining a longitudinal axis and a longitudinal passage extending along the longitudinal axis from the proximal end to the distal end, the longitudinal passage adapted to receive a second instrument through the tubular body, the tubular body further defining a first longitudinal slot and a second longitudinal slot opposite the first longitudinal slot, the first longitudinal slot and the second longitudinal slot terminating at the distal end of the tubular body and forming a transverse passage through the tubular body, the transverse passage adapted to receive a longitudinal fixation element through the tubular body, the tubular body further comprising a first extension and a second extension opposite the first extension, the first extension separated from the second extension by the first longitudinal slot and the second longitudinal slot, the first extension comprising a first pivot arm for detachably connecting the surgical instrument to a first connector on a vertebral anchor and a second pivot arm for detachably connecting the surgical instrument to a second connector on the vertebral anchor, the first pivot arm having a first activation end and a first attachment end opposite the first activation end, and the second pivot arm having a second activation end and a second attachment end opposite the second activation end, the first pivot arm defining a first anti-splaying slot extending from the first activation end to the first attachment end, and the second pivot arm defining a second anti-splaying slot extending from the second activation end to the second attachment end, at least one of the first anti-splaying slot and the second anti-splaying slot being open in a radial direction toward the longitudinal axis and open to the longitudinal passage to receive an anti-splaying element on the second instrument.

2. The surgical instrument of claim 1, wherein the tubular body defines a first elongated aperture, at least a portion of which extends into the first extension, and a second elongated aperture, at least a portion of which extends into the second extension.

3. The surgical instrument of claim 2, wherein the first pivot arm is pivotally mounted in the first elongated aperture and the second pivot arm is pivotally mounted in the second elongated aperture.

4. The surgical instrument of claim 2, wherein the first pivot arm is mounted in the first elongated aperture by a first pivot connection, and the second pivot arm is mounted in the second elongated aperture by a second pivot connection.

5. The surgical instrument of claim 4, wherein the first activation end of the first pivot arm is connected to the first attachment end by a first dog leg section, and the second activation end of the second pivot arm is connected to the second attachment end by a second dog leg portion.

6. The surgical instrument of claim 5, wherein the first anti-splaying slot defines a first aperture in the first dog leg section facing the proximal end of the tubular body, the first aperture configured to axially receive a first anti-splaying element on the second instrument, and wherein the second anti-splaying slot defines a second aperture in the second dog leg section facing the proximal end of the tubular body, the second aperture configured to axially receive a second anti-splaying element on the second instrument.

7. The surgical instrument of claim 5, wherein the first pivot arm is connected to the first pivot connection at the first dog leg section, and the second pivot arm is connected to the second pivot connection at the second dog leg section.

8. The surgical instrument of claim 1, wherein the first pivot arm and the second pivot arm are pivotally displaceable relative to the tubular body between an attachment position, in which the first attachment end and the second attachment end are attachable to the vertebral anchor, and a release position, in which the first attachment end and the second attachment end are removable from the vertebral anchor.

9. The surgical instrument of claim 8, wherein the first activation end of the first pivot arm is closer to the longitudinal axis in the release position than in the attachment position, and the second activation end of the second pivot arm is closer to the longitudinal axis in the release position than in the attachment position.

10. The surgical instrument of claim 8, further comprising a first biasing element that biases the first pivot arm toward the attachment position and a second biasing element that biases the second pivot arm toward the attachment position.

11. The surgical instrument of claim 10, wherein the first biasing element comprises a first spring that exerts a first radially outward biasing force on the first activation end of the first pivot arm, and the second biasing element comprises a second spring that exerts a second radially outward biasing force on the second activation end of the second pivot arm.

12. The surgical instrument of claim 11, wherein the first pivot arm and the second pivot arm are pivotally displaceable against the first radially outward biasing force and the second radially outward biasing force, and toward the release position, in response to radially inward forces applied to the first activation end and the second activation end of the first pivot arm and the second pivot arm, respectively.

13. The surgical instrument of claim 11, wherein pivotal displacement of the first pivot arm and the second pivot arm to the release position compresses the first spring and the second spring under stored energy.

14. The surgical instrument of claim 11, wherein the first activation end of the first pivot arm comprises a first recess that receives the first spring, and the second activation end of the second pivot arm defines a second recess that receives the second spring.

15. The surgical instrument of claim 8, wherein the first activation end of the first pivot arm projects radially outwardly from the first aperture when the first pivot arm is in the attachment position, and the second activation end of the second pivot arm projects radially outwardly from the second aperture when the second pivot arm is in the attachment position.

16. The surgical instrument of claim 8, wherein the first aperture comprises a first stop for limiting pivotal displacement of the first pivot arm beyond the attachment position and a second stop for limiting pivotal displacement of the first pivot arm beyond the release position.

17. The surgical instrument of claim 8, wherein the first attachment end of the first pivot arm extends into the longitudinal passage when the first pivot arm is displaced to the attachment position, and the second attachment end of the second pivot arm extends into the longitudinal passage when the second pivot arm is displaced to the attachment position.

18. The surgical instrument of claim 8, wherein the first attachment end of the first pivot arm is outside of the longitudinal passage when the first pivot arm is displaced to the release position, and the second attachment end of the second pivot arm is outside of the longitudinal passage when the second pivot arm is displaced to the release position.

19. The surgical instrument of claim 1, wherein the proximal end of the tubular body comprises a connection element for axially guiding the second instrument inside the longitudinal passage.

20. A surgical instrument for correcting spinal deformities, the surgical instrument comprising a tubular body having a proximal end, a distal end opposite the proximal end, and a midsection extending between the proximal end and the distal end, the tubular body defining a longitudinal axis and a longitudinal passage extending along the longitudinal axis from the proximal end to the distal end, the longitudinal passage adapted to receive a second instrument through the tubular body, the tubular body further defining a first longitudinal slot and a second longitudinal slot opposite the first longitudinal slot, the first longitudinal slot and the second longitudinal slot terminating at the distal end of the tubular body and forming a transverse passage through the tubular body, the transverse passage adapted to receive a longitudinal fixation element through the tubular body, the tubular body further comprising a first extension and a second extension opposite the first extension, the first extension separated from the second extension by the first longitudinal slot and the second longitudinal slot, the first extension comprising a first pivot arm for detachably connecting the surgical instrument to a first connector on a vertebral anchor and a second pivot arm for detachably connecting the surgical instrument to a second connector on the vertebral anchor, the first pivot arm having a first activation end and a first attachment end opposite the first activation end, and the second pivot arm having a second activation end and a second attachment end opposite the second activation end, the first pivot arm defining a first anti-splaying slot extending from the first activation end to the first attachment end, the first anti-splaying slot being open to the longitudinal passage and adapted to receive a first anti-splaying element on the second instrument, and the second pivot arm defining a second anti-splaying slot extending from the second activation end to the second attachment end, the second anti-splaying slot being open to the longitudinal passage and adapted to receive a second anti-splaying element on the second instrument, wherein the first pivot arm and the second pivot arm are pivotally displaceable relative to the tubular body between an attachment position, in which the first attachment end and the second attachment end are attachable to the vertebral anchor, and a release position, in which the first attachment end and the second attachment end are removable from the vertebral anchor, and wherein the surgical instrument further comprises a first biasing element that biases the first pivot arm toward the attachment position and a second biasing element that biases the second pivot arm toward the attachment position.

21. The surgical instrument of claim 20, wherein the first biasing element comprises a first spring that exerts a first radially outward biasing force on the first activation end of the first pivot arm, and the second biasing element comprises a second spring that exerts a second radially outward biasing force on the second activation end of the second pivot arm.

22. The surgical instrument of claim 21, wherein the first pivot arm and the second pivot arm are pivotally displaceable against the first radially outward biasing force and the second radially outward biasing force, and toward the release position, in response to radially inward forces applied to the first activation end and the second activation end of the first pivot arm and the second pivot arm, respectively.

23. The surgical instrument of claim 21, wherein pivotal displacement of the first pivot arm and the second pivot arm to the release position compresses the first spring and the second spring under stored energy.

24. The surgical instrument of claim 21, wherein the first activation end of the first pivot arm comprises a first recess that receives the first spring, and the second activation end of the second pivot arm defines a second recess that receives the second spring.

25. A surgical instrument for correcting spinal deformities, the surgical instrument comprising a tubular body having a proximal end, a distal end opposite the proximal end, and a midsection extending between the proximal end and the distal end, the tubular body defining a longitudinal axis and a longitudinal passage extending along the longitudinal axis from the proximal end to the distal end, the longitudinal passage adapted to receive a second instrument through the tubular body, the tubular body further defining a first longitudinal slot and a second longitudinal slot opposite the first longitudinal slot, the first longitudinal slot and the second longitudinal slot terminating at the distal end of the tubular body and forming a transverse passage through the tubular body, the transverse passage adapted to receive a longitudinal fixation element through the tubular body, the tubular body further comprising a first extension and a second extension opposite the first extension, the first extension separated from the second extension by the first longitudinal slot and the second longitudinal slot, the first extension comprising a first pivot arm for detachably connecting the surgical instrument to a first connector on a vertebral anchor and a second pivot arm for detachably connecting the surgical instrument to a second connector on the vertebral anchor, the first pivot arm having a first activation end and a first attachment end opposite the first activation end, and the second pivot arm having a second activation end and a second attachment end opposite the second activation end, the first pivot arm defining a first anti-splaying slot extending from the first activation end to the first attachment end, the first anti-splaying slot being open to the longitudinal passage and adapted to receive a first anti-splaying element on the second instrument, and the second pivot arm defining a second anti-splaying slot extending from the second activation end to the second attachment end, the second anti-splaying slot being open to the longitudinal passage and adapted to receive a second anti-splaying element on the second instrument, wherein the first pivot arm and the second pivot arm are pivotally displaceable relative to the tubular body between an attachment position, in which the first attachment end and the second attachment end are attachable to the vertebral anchor, and a release position, in which the first attachment end and the second attachment end are removable from the vertebral anchor, and wherein the first attachment end of the first pivot arm extends into the longitudinal passage when the first pivot arm is displaced to the attachment position, and the second attachment end of the second pivot arm extends into the longitudinal passage when the second pivot arm is displaced to the attachment position.

* * * * *